(12) United States Patent
Earle (10) Patent No.: US 7,878,811 B2
(45) Date of Patent: Feb. 1, 2011

(54) METHOD AND SYSTEM FOR PROVIDING TIMELY PERFORMANCE EVALUATIONS TO MEDICAL STUDENTS OR TRAINEES

(75) Inventor: David B. Earle, 9 Blueberry Hill Rd., Longmeadow, MA (US) 01106

(73) Assignee: David B. Earle, Longmeadow, MA (US)

( * ) Notice: Subject to any disclaimer, the term of this patent is extended or adjusted under 35 U.S.C. 154(b) by 849 days.

(21) Appl. No.: 11/402,163

(22) Filed: Apr. 10, 2006

(65) Prior Publication Data
US 2006/0229913 A1    Oct. 12, 2006

Related U.S. Application Data

(60) Provisional application No. 60/670,070, filed on Apr. 11, 2005.

(51) Int. Cl.
G09B 23/28 (2006.01)
G09B 19/00 (2006.01)

(52) U.S. Cl. .................. 434/262; 434/219; 434/236; 434/267; 434/308; 434/322

(58) Field of Classification Search ............... 434/236, 434/350, 262, 266, 219, 267
See application file for complete search history.

(56) References Cited

U.S. PATENT DOCUMENTS

| | | | |
|---|---|---|---|
| 4,360,345 A * | 11/1982 | Hon ........................... 434/262 |
| 5,842,173 A * | 11/1998 | Strum et al. ................... 705/1 |
| 5,882,206 A * | 3/1999 | Gillio ......................... 434/262 |
| 6,078,894 A * | 6/2000 | Clawson et al. ............... 705/11 |
| 6,106,459 A * | 8/2000 | Clawson ...................... 600/300 |
| 6,350,239 B1 | 2/2002 | Ohad et al. |
| 6,546,230 B1 * | 4/2003 | Allison ....................... 434/350 |
| 6,616,453 B2 * | 9/2003 | Kouba et al. ................. 434/219 |
| 6,734,958 B1 | 5/2004 | MacKinnon et al. |
| 6,739,877 B2 * | 5/2004 | Bailey et al. ................. 434/262 |
| 6,830,180 B2 | 12/2004 | Walsh |
| 6,849,045 B2 | 2/2005 | Iliff |
| 6,850,889 B1 | 2/2005 | Zayas, Jr. |
| 6,858,003 B2 | 2/2005 | Evans et al. |
| 6,863,536 B1 | 3/2005 | Fisher et al. |
| 6,918,771 B2 | 7/2005 | Arington et al. |
| 7,011,528 B2 * | 3/2006 | Tweet et al. ................. 434/262 |

(Continued)

OTHER PUBLICATIONS

Feldman, Henry M.D., et al., "ResEval: A Web-based Evaluation System for Internal Medicine House Staff", WWW.2004, May 17-22, 2004, New York, New York, USA.

*Primary Examiner*—Xuan M Thai
*Assistant Examiner*—Kang Hu
(74) *Attorney, Agent, or Firm*—Holland & Bonzagni, P.C.; Mary R. Bonzagni, Esq.

(57) ABSTRACT

A method and system for providing performance evaluations, on a timely basis, to students or trainees, is provided. In one contemplated embodiment, the inventive method and system are used in health care training programs to form an information feedback loop whereby clinical and simulated clinical performance evaluations are inputted, or gathered and stored, and then made available to the health care practitioner and to his/her educator(s) throughout the health care training program thereby increasing the effectiveness of the training program by allowing the program to be continuously tailored to address the needs of the health care practitioner.

19 Claims, 7 Drawing Sheets

U.S. PATENT DOCUMENTS

| | | | |
|---|---|---|---|
| 7,457,581 B2 * | 11/2008 | Stout et al. | 434/353 |
| 2003/0031993 A1 * | 2/2003 | Pugh | 434/262 |
| 2005/0170323 A1 * | 8/2005 | Jarrell et al. | 434/262 |
| 2005/0186549 A1 * | 8/2005 | Huang | 434/322 |
| 2008/0015418 A1 * | 1/2008 | Jarrell et al. | 600/300 |
| 2009/0004638 A1 * | 1/2009 | Stout et al. | 434/353 |

* cited by examiner

Resident Case Log

Attending 1: [ ] Attending 2: [ ] Procedure: [ ] [ ]
Resident: [ ] Program: [ ] Role: [ ] Code: [ ]
Category: [ ] Description: [ ] (mm/dd/yyyy)
Med Rec: [ ]

☐ Open ☐ Laparoscopic ☐ Lap Assisted ☐ Lap To Open
☐ Attending Not Available

Resident Evaluation

Pre-Op

1. Patient Information (including pre-op) ○ Well Informed ○ Somewhat Informed ○ Knows a Few Facts ○ Knows Nothing ○ N/A
2. Prepared for case (disease) ○ Well Informed ○ Somewhat Informed ○ Knows a Few Facts ○ Knows Nothing ○ N/A
3. Prepared for case (technical) ○ Well Informed ○ Somewhat Informed ○ Knows a Few Facts ○ Knows Nothing ○ N/A
4. In room for intubation ○ Yes ○ No ○ N/A

OR Skills

──── Laparoscopic ──── ──── Open ────

1. Appropriate tissue handling
2. Secure knot tying
3. Demonstrates dexterity while knot tying
4. Demonstrates dexterity with instruments
5. Efficient planning and movements
6. Independently moves operation forward
7. Equipment troubleshooting ability  ○ Always  ○ Usually  ○ Occasionally  ○ Never  ○ N/A

Key
A – Always
O – Occasionally
U – Usually
N – Never
NN – N/A

Comments: [ ]

Overall resident performance
○ Excellent  ○ Appropriate for level  ○ Needs work *  ○ Poor *    * Requires Comment

Overall

Resident Participation
☐ Resident Not Available
Resident's Estimate [ ] %
Attending Estimate [ ] %

[Save Evaluation]  [Clear Form]

Resident Report

Resident: _____________

Total Number of cases: _____  Start Date: __________ (MM/DD/YYYY)

Number Attending not Available: _____  End Date: __________

Percent: _____

Program Year:
1
2
3
4
5
6

By default all program years will be included in the percentages unless a specific year or years are selected.

[Load]  [Attending List]  [Comments]  [Run Report]  [Exit]

Pre-Op

|  | Well Informed | Somewhat Informed | Knows a Few Facts | Knows Nothing | N/A |
|---|---|---|---|---|---|
| 1. Patient Information (including pre-op note) | ☐ | ☐ | ☐ | ☐ | ☐ |
| 2. Prepared for case (disease) | ☐ | ☐ | ☐ | ☐ | ☐ |
| 3. Prepared for case (technical) | ☐ | ☐ | ☐ | ☐ | ☐ |
| 4. In room for intubation | ☐ | ☐ | ☐ | ☐ | ☐ |

Average ☐

[Chart]

OR Skills

| | Laparoscopic | | | | | Open | | | | |
|---|---|---|---|---|---|---|---|---|---|---|
| | Always | Occasion | Usually | Never | N/A | Always | Occasion | Usually | Never | N/A |
| 1. Appropriate tissue handling | ☐ | ☐ | ☐ | ☐ | ☐ | ☐ | ☐ | ☐ | ☐ | ☐ |
| 2. Secure knot tying | ☐ | ☐ | ☐ | ☐ | ☐ | ☐ | ☐ | ☐ | ☐ | ☐ |
| 3. Demonstrates dexterity while knot tying | ☐ | ☐ | ☐ | ☐ | ☐ | ☐ | ☐ | ☐ | ☐ | ☐ |
| 4. Demonstrates dexterity with instruments | ☐ | ☐ | ☐ | ☐ | ☐ | ☐ | ☐ | ☐ | ☐ | ☐ |
| 5. Efficient planning and movements | ☐ | ☐ | ☐ | ☐ | ☐ | ☐ | ☐ | ☐ | ☐ | ☐ |
| 6. Independently moves operation forward | ☐ | ☐ | ☐ | ☐ | ☐ | ☐ | ☐ | ☐ | ☐ | ☐ |
| 7. Equipment troubleshooting ability | ☐ | ☐ | ☐ | ☐ | ☐ | ☐ | ☐ | ☐ | ☐ | ☐ |

Average ☐  ☐

[Chart]  [Chart]

*FIG. 4*

Baystate Health System
Resident Evaluation System
Resident Report
Erica
Date Range: All          Program Year: All
         Total Number of Cases: 14

Pre-Op

| | Well Informed | Somewhat Informed | Knows a Few Facts | Knows Nothing | N/A |
|---|---|---|---|---|---|
| 1. Patient Information (including pre-op note) | 64% | 7% | 7% | 21% | |
| 2. Prepared for case (disease) | 43% | 29% | | | 29% |
| 3. Prepared for case (technical) | 43% | 21% | | | 29% |
| 4. In room for intubation | 79% | 21% | | | |
| Average | 57% | 20% | 4% | 5% | 14% |

OR Skills

| | Laparoscopic | | | | | Open | | | | |
|---|---|---|---|---|---|---|---|---|---|---|
| | Always | Occasion | Usually | Never | N/A | Always | Occasion | Usually | Never | N/A |
| 1. Appropriate tissue handling | 7% | 43% | | | 50% | 14% | 64% | | | 21% |
| 2. Secure knot tying | 7% | | 7% | | 86% | 43% | 36% | | | 21% |
| 3. Demonstrates dexterity while knot tying | | 14% | | | 86% | 21% | 50% | 7% | 7% | 14% |
| 4. Demonstrates dexterity with instruments | 50% | 21% | | | 29% | 14% | 64% | | 7% | 14% |
| 5. Efficient planning and movements | 36% | 36% | | | 29% | 7% | 50% | 14% | 7% | 21% |
| 6. Independently moves operation forward | 7% | 50% | | 14% | 29% | 7% | 14% | 50% | 7% | 29% |
| 7. Equipment troubleshooting ability | 7% | 29% | | | 64% | | | | | |
| Average | 2% | 20% | 21% | 3% | 53% | 18% | 46% | 12% | 4% | 20% |

Attending List     Nbr Attending Not Available: 0          Percent: 0%

| Attending Physician | Nbr Cases | Cases Completed | Percent Completed |
|---|---|---|---|
| Chang, Lisa | 2 | 2 | 100% |
| Earle, David | 9 | 9 | 100% |
| Sullivan, Michael | 2 | 2 | 100% |
| Brown, Brenda | 1 | 1 | 100% |

METHOD AND SYSTEM FOR PROVIDING TIMELY PERFORMANCE EVALUATIONS TO MEDICAL STUDENTS OR TRAINEES

RELATED APPLICATION

This application claims priority from U.S. Provisional Patent Application Ser. No. 60/670,070, filed Apr. 11, 2005.

FIELD OF THE INVENTION

The present invention generally relates to a method and system for providing timely performance evaluations to students or trainees, and more specifically relates to a method and system for use in health care training programs that serve to provide timely performance evaluations to health care practitioners including medical students and surgical residents. In one contemplated embodiment, an information feedback loop is formed by the subject invention whereby clinical and simulated clinical performance evaluations are inputted, or gathered and stored, and then made available to the health care practitioner and to his/her educator(s) throughout the health care training program thereby increasing the effectiveness of the training program by allowing the program to be continuously tailored to address the needs of the health care practitioner.

BACKGROUND AND SUMMARY OF THE INVENTION

Current surgical educational curricula are composed almost exclusively of apprenticeship style education, and lectures. With a recent mandated decrease in residency work hours, and no decrease in the number and content of the lectures, there is effectively a decrease in the apprenticeship program, thus a decrease in the amount of training, and possibly then, the quality of the final product of training—a general surgeon.

The present invention serves to address this deficiency by generally providing a method and system for use in training and performance programs that involve complex tasks (e.g., medical, aerospace, and aviation training and performance programs) that provide timely performance evaluations to students or trainees. In one contemplated embodiment of the present invention, the method and system is used in surgical training programs to provide near immediate feedback to surgical residents on their operative skills and overall operative performance after each resident-assisted surgical procedure, thereby enhancing resident education, improving the quality of patient care during the resident education process, and making utilization of the operating room training environment more efficient.

The Internal Medicine residency training program at NYU School of Medicine recently implemented a web-based evaluation system, which attempts to address a related problem concerning residency training. This web-based evaluation system is directed toward the following core areas of residency assessment: Clinical Interviewing, Physical Examination, Oral Case Presentations, Differential Diagnosis, Interpretation of Data, Diagnostic Plans, Therapeutic Plans, Teaching Skills, Procedures, and Professionalism. Modules containing evaluation questions are built into the system, with the system reportedly automatically building an appropriate evaluation form from the available modules, on-the-fly, based on the level of training of the evaluator and the resident and the type of assessment. More specifically, after logging into the system, an evaluator selects a resident to evaluate. The system, which is reportedly aware of the training level of both of these individuals, presents the evaluator with a filtered list of evaluation forms that are appropriate to their relationship. The evaluator selects and completes a form, the module-based data is collected and pooled for analysis and summary, and the analysis and summary made available to the resident. This web-based evaluation system, however, does not address, nor serve to provide, among other things, timely operative performance evaluations to surgical trainees or residents and their educators.

The present invention, which also serves to address the deficiency of the above-referenced web-based evaluation system, generally provides a computer-based method for providing timely complex task skills or performance evaluations to students or trainees, the method comprising:

(a) providing at least one computer station operable by trained educators for inputting their evaluations of the complex task performance of trainees and further operable by the trainees, as well as, the trained educators and other educators, for viewing the inputted evaluations;

(b) further providing at least one computer and at least one computer database accessible by the computer(s) for storing information including the trained educator evaluations, wherein the computer comprises memory means and one or more computer programs stored therein suitable for the management and manipulation of the information that is directed into or out of the computer database and/or stored therein;

(c) arranging for the trainees to perform complex tasks under a trained educator's direct supervision;

(d) evaluating each trainee's complex task performance and upon completion of each such task, entering the trained educator's evaluation of the trainee's performance at the computer station and storing the evaluation in the computer database such that the evaluation is accessible by the trainee;

(e) for each such trainee, generating and displaying reports showing the trainee's complex task performance trends over time; and optionally, (f) for each group or team of such trainees, generating and displaying reports showing the trainee group or team's complex task performance trends over time.

In a preferred embodiment, the inventive method further comprises: providing a communications link between the computer(s) and one or more simulation tools or devices used by the trainees; arranging for trainees to use the one or more simulation devices; importing results from the one or more simulation devices used by the trainees into the computer(s) and storing same in the computer database(s), such that the results are accessible by the trainees, the trained educators and other educators; and using the results from the one or more simulation devices to guide trainee education and training.

In a more preferred embodiment, the inventive computer-based method provides timely skills or performance evaluations to health care practitioners. In this more preferred embodiment, the inventive method may optionally integrate both clinical and simulated clinical performance evaluations.

In yet a more preferred embodiment, the inventive computer-based method provides both timely clinical operative and simulated clinical operative performance evaluations to surgical residents. In this more preferred embodiment, the inventive method may further serve to reduce the risk of human error in the operating room by verifying the identity of a patient and scheduled surgical procedure to be performed on that patient and to provide, among other things, operating room efficiency and safety assessments, in addition to, providing timely surgical resident operative performance evaluations. More specifically, the inventive method may further comprise:

(a) providing a communications link between the computer (s) and a hospital database containing patient information; and for each surgical procedure scheduled to be performed in an operating room, (b) entering into the computer station a patient identifier which identifies the patient on which the scheduled surgical procedure is to be performed; and if the patient identifier entered into the computer station matches an identifier for that patient stored in the hospital database, (c) checking the scheduled surgical procedure against the surgical procedure for that patient that is stored in the hospital database; and if the scheduled surgical procedure for the patient matches the surgical procedure for that patient stored in the hospital database, (d) performing the surgical procedure on the patient; and optionally, for each patient on which a resident-assisted surgical procedure has been performed in the operating room, and using the patient identifier, (e) collecting from the hospital database clinical parameters such as operating room time, case cost, length of stay, complications, and the like, storing this information in the computer database, and generating and displaying reports assessing, among other things, the operating room's efficiency and safety which are accessible by appropriate hospital personnel.

The present invention further generally provides a system for use in complex task training and performance programs that provides timely skills or performance evaluations to students or trainees, which system comprises:

(a) at least one computer station operable by trained educators for inputting their evaluations of the complex task performance of trainees and further operable by the trainees, as well as, the trained educators and other educators, for viewing the inputted evaluations; and (b) at least one computer and a computer database accessible by the computer for storing information including trained educator evaluations, wherein the computer comprises memory means and one or more computer programs stored therein suitable for the management and manipulation of the information that is directed into or out of the computer database and/or stored therein.

In a preferred embodiment, the inventive system further comprises: one or more complex task simulation devices; and a communications link between the computer(s) and the one or more simulation devices.

In a more preferred embodiment, the inventive system is used for providing timely skills or performance evaluations to health care practitioners. In this more preferred embodiment, the inventive system may optionally further comprise one or more simulation devices and a communications link between the computer(s) and the one or more simulation devices.

In yet a more preferred embodiment, the inventive system is used for providing both timely clinical operative and simulated clinical operative performance evaluations to surgical residents. In this more preferred embodiment, the inventive system may also aid in reducing the risk of human error in the operating room by verifying the identity of a patient and scheduled surgical procedure to be performed on that patient, and hence provide, among other things, operating room efficiency and safety assessments, in addition to, timely surgical resident operative performance evaluations, and therefore may further comprise a communications link between the computer(s) and a hospital database containing patient information.

Other features and advantages of the invention will be apparent to one of ordinary skill from the following detailed description and drawings. Unless otherwise defined, all technical and scientific terms used herein have the same meaning as commonly understood by one of ordinary skill in the art to which this invention belongs. All publications, patent applications, patents and other references mentioned herein are incorporated by reference in their entirety. In case of conflict, the present specification, including definitions, will control.

BRIEF DESCRIPTION OF THE DRAWINGS

In the course of the description which follows, reference is made to the drawings, in which.

BEST MODE FOR CARRYING OUT THE INVENTION

As noted above, the preferred system and method of the present invention, which serve to provide near immediate feedback to health care practitioners on their skills and overall performance after each practitioner-assisted health care or medical procedure, enhances practitioner education, improves the quality of patient care during the practitioner education process, and makes utilization of the training environment more efficient. The term "health care practitioner", as used herein, is not limited, and includes everyone from medical students, surgical residents, doctors, dentists, emergency medical technicians, and physical therapists, to physician assistants, radiology technologists, respiratory therapists, optometrists, podiatrists, and speech pathologists.

Figure 1:
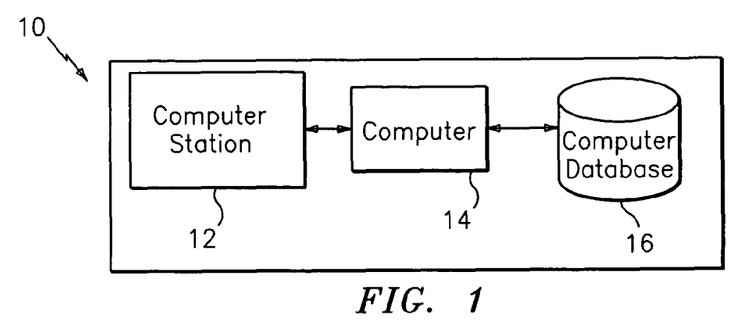
FIG. 1 is a simplified component diagram of the system of the present invention.

Referring now to FIG. 1, a preferred embodiment of the inventive system for providing timely skills or performance evaluations to health care practitioners is shown generally at 10. System 10 may be regarded as generally including at least one computer station 12 (equipped with a terminal or other access device), at least one computer 14, and a computer database 16 accessible by the computer 14 for storing information including trained educator evaluations. The terminal or other access device of computer station(s) 12 is operable with a user interface for accessing the computer(s) 14 and database 16. One or more computer programs reside in and are executable by the computer(s) 14 for managing the storage of information and for manipulating and retrieving the information that is directed into or out of the computer database 16 and/or stored therein.

The computer(s) 14 and the computer database 16 may reside in the same physical location as the computer station(s) 12 (i.e., the operating room) and may be regarded as part of the computer station(s) 12. The computer(s) 14 and the computer database 16 may also reside in a location remote from where the computer station(s) 12 is/are located.

In a preferred embodiment, system 10 includes a plurality of computer stations 12. Generally, preferred system 10 is an Intranet-based system that allows for interconnection and communication between each of the stations 12. System 10, however, is equally adaptable to other communication environments such as the Internet. For example, the at least one computer 14 of system 10 may be one or more server computers that act as gateways for Internet access. The server computer(s) 14 may be adapted to support a website that allows for remote access to the server computer(s) 14 and the computer database 16.

By way of the computer-based method of the present invention, a health care or medical procedure would be performed by a health care practitioner under the direct supervision of a trained educator. Upon completion of the procedure, the trained educator would access system 10 through the user interface of computer station 12 and input his/her evaluation of the skills or performance of the health care practitioner. The inputted evaluation, preferably in the form of a completed questionnaire, is then directed to the computer 14 for storage in the database 16. Upon entry into the database 16, this information becomes accessible to the health care practitioner, the trained educator and other educators. As described in more detail below, data may be downloaded, reviewed or otherwise communicated to the health care practitioner and his/her educators at the computer station(s) 12. The benefits inherent in the near immediate or instantaneous feedback from the trained educator include, for example, the ability of trained educators to capture impressions that don't rely on recall and to be provided with the tools needed to customize future training exercises to focus on any weaknesses or problem areas observed during each health care practitioner-assisted procedure.

In a preferred embodiment, the inventive computer-based method provides timely operative skills and overall operative performance evaluations to surgical residents. Key areas evaluated by a trained surgeon in this embodiment would include the resident's cognitive skills for treating the patient (e.g., the extent to which the resident was informed about the patient and the technical and disease related issues of the particular case), and the resident's operative skills.

Figure 2:
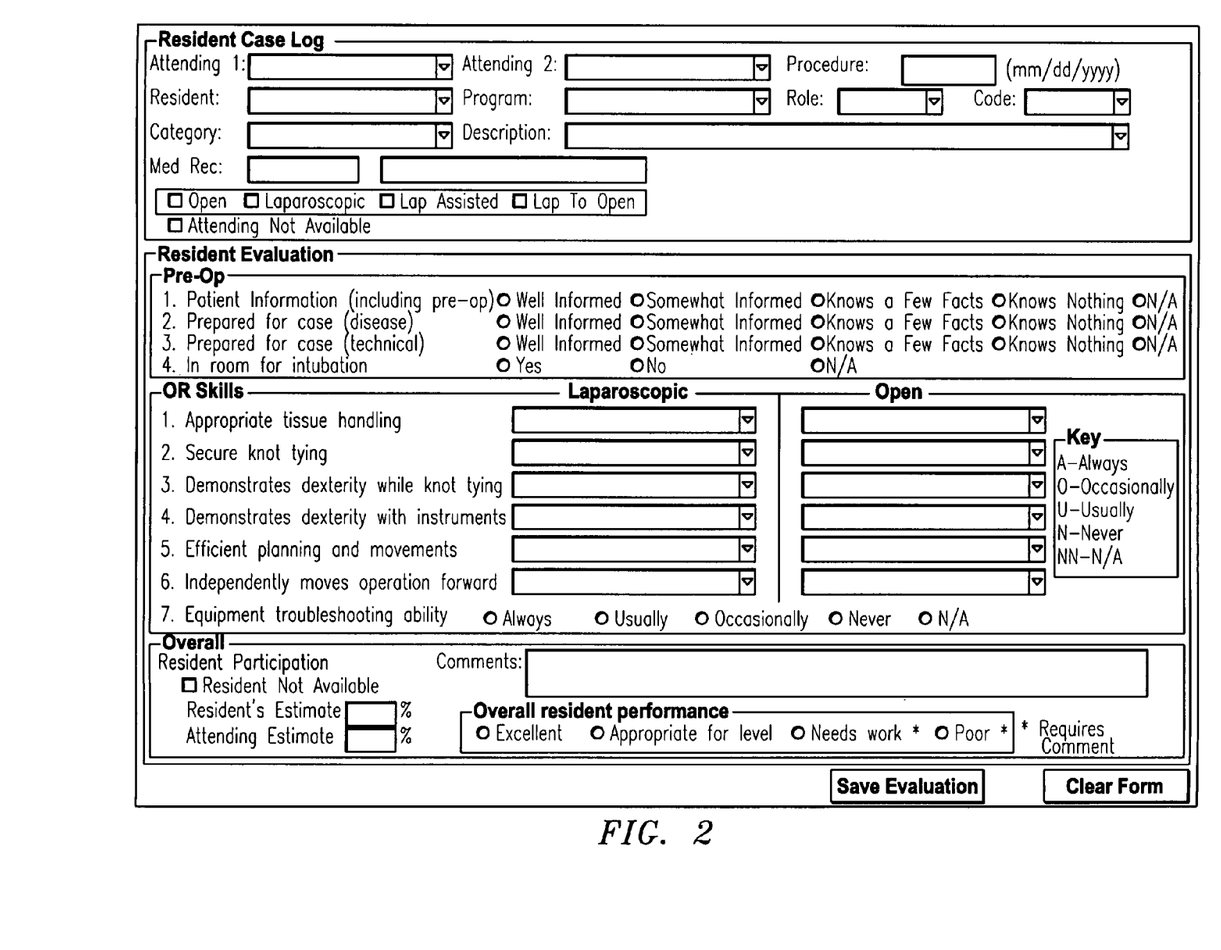
FIG. 2 illustrates a user interface screen display in the form of a resident evaluation form or questionnaire relating to laparoscopic skills assessment, which is suitable for use in the present invention.
Figure 3:
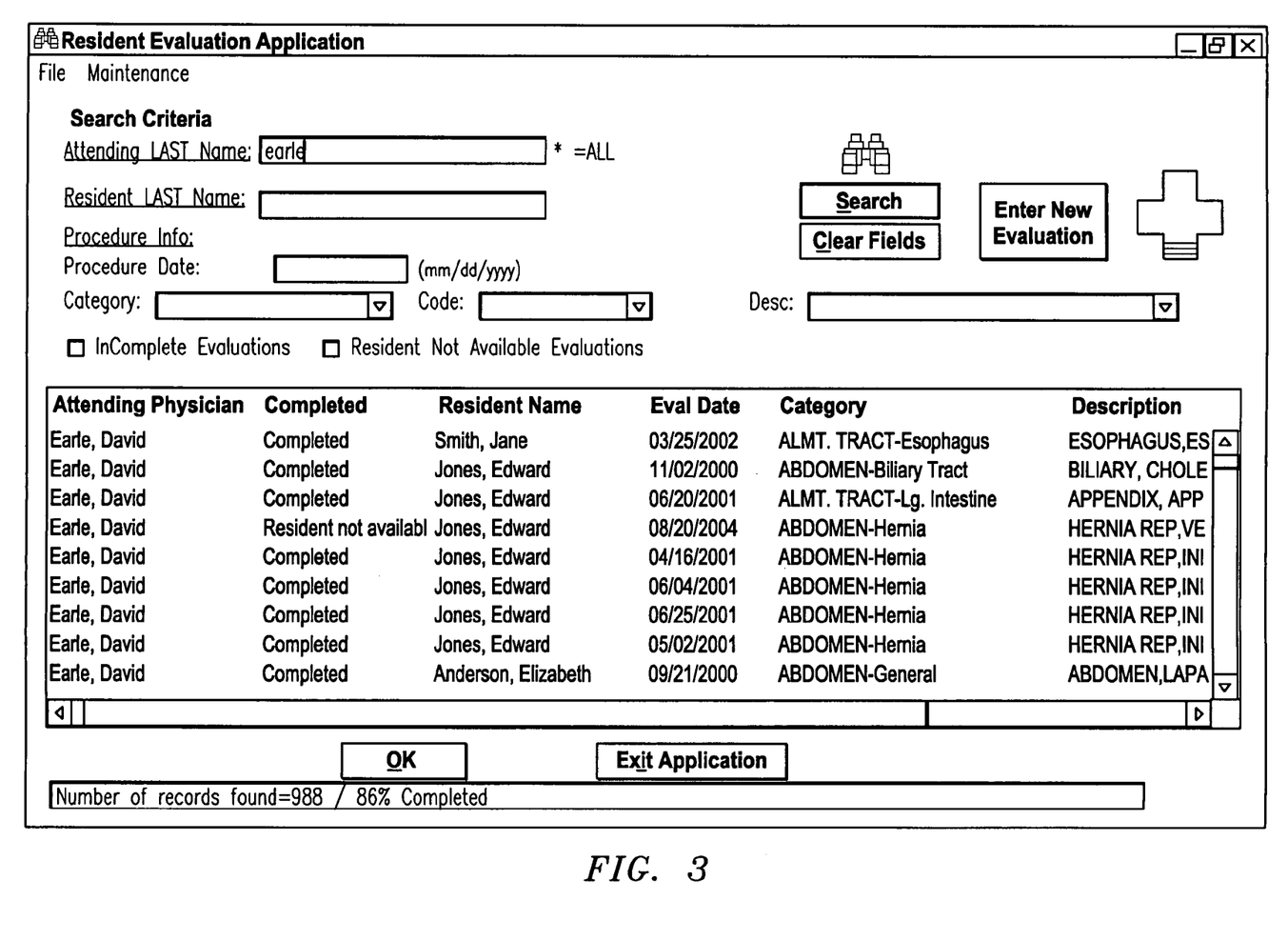
FIG. 3 illustrates a report generated by a preferred embodiment of the present inventive system, obtained by field searching a trained surgeon's last name, and showing a list of resident-assisted surgical procedures supervised by that trained surgeon.
Figure 4:
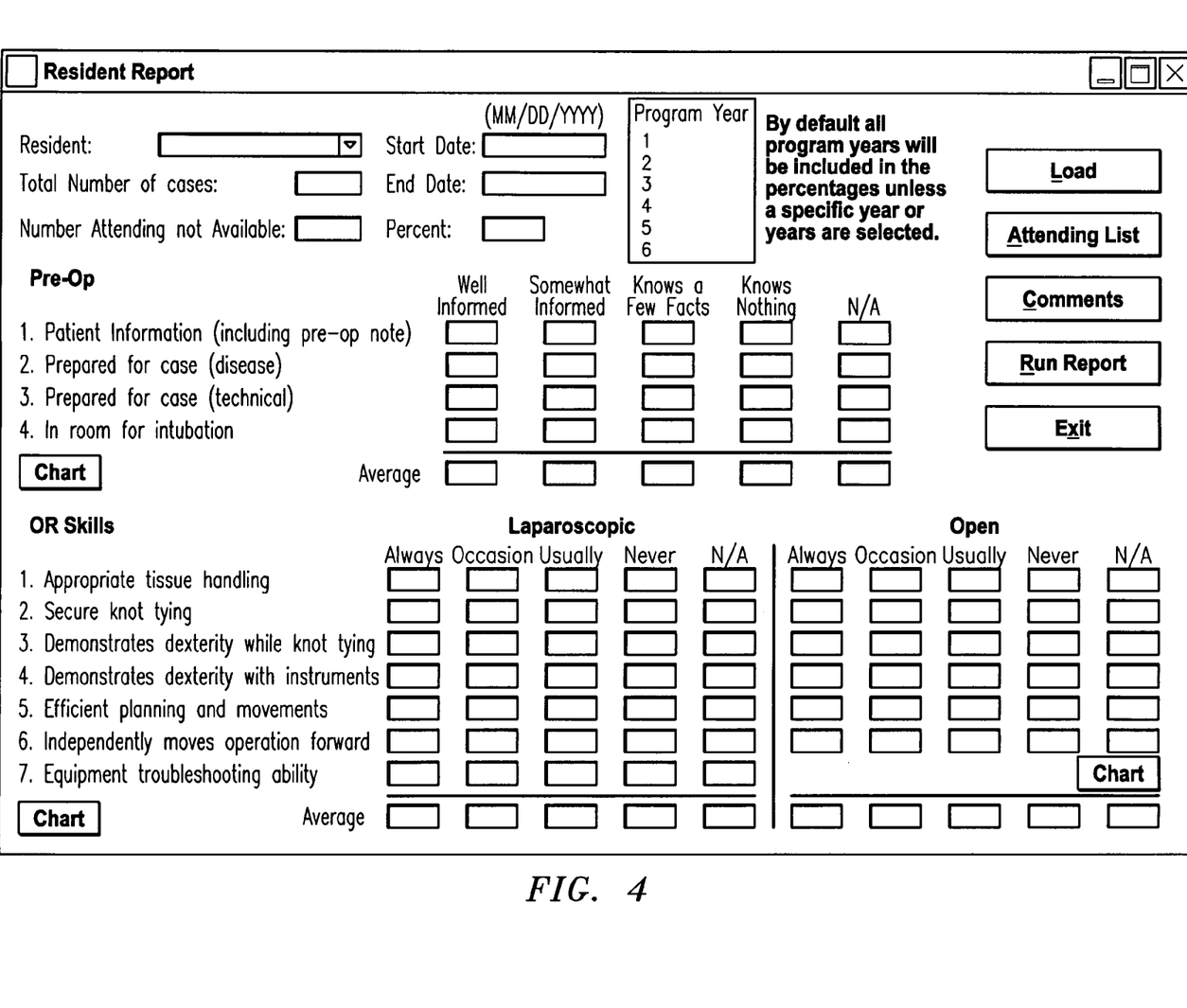
FIG. 4 illustrates a blank resident report form, completion of which is effected by the inventive system upon field searching resident name and, optionally, time period.
Figure 5:
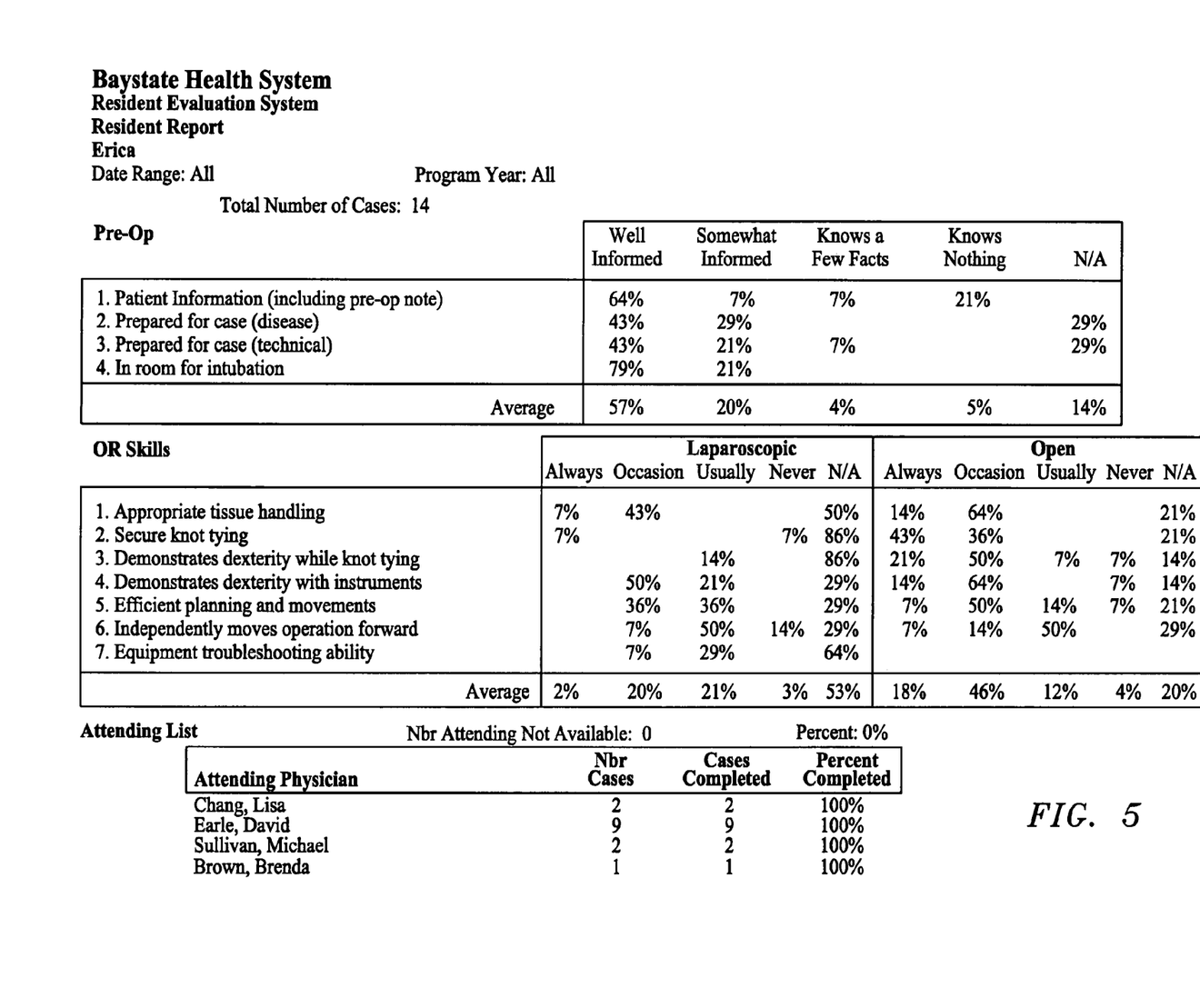
FIG. 5 illustrates an alternative presentation or display of a resident report showing calculated average resident performance levels in assessed performance categories, which may also be generated by the present inventive system.
Figure 6:
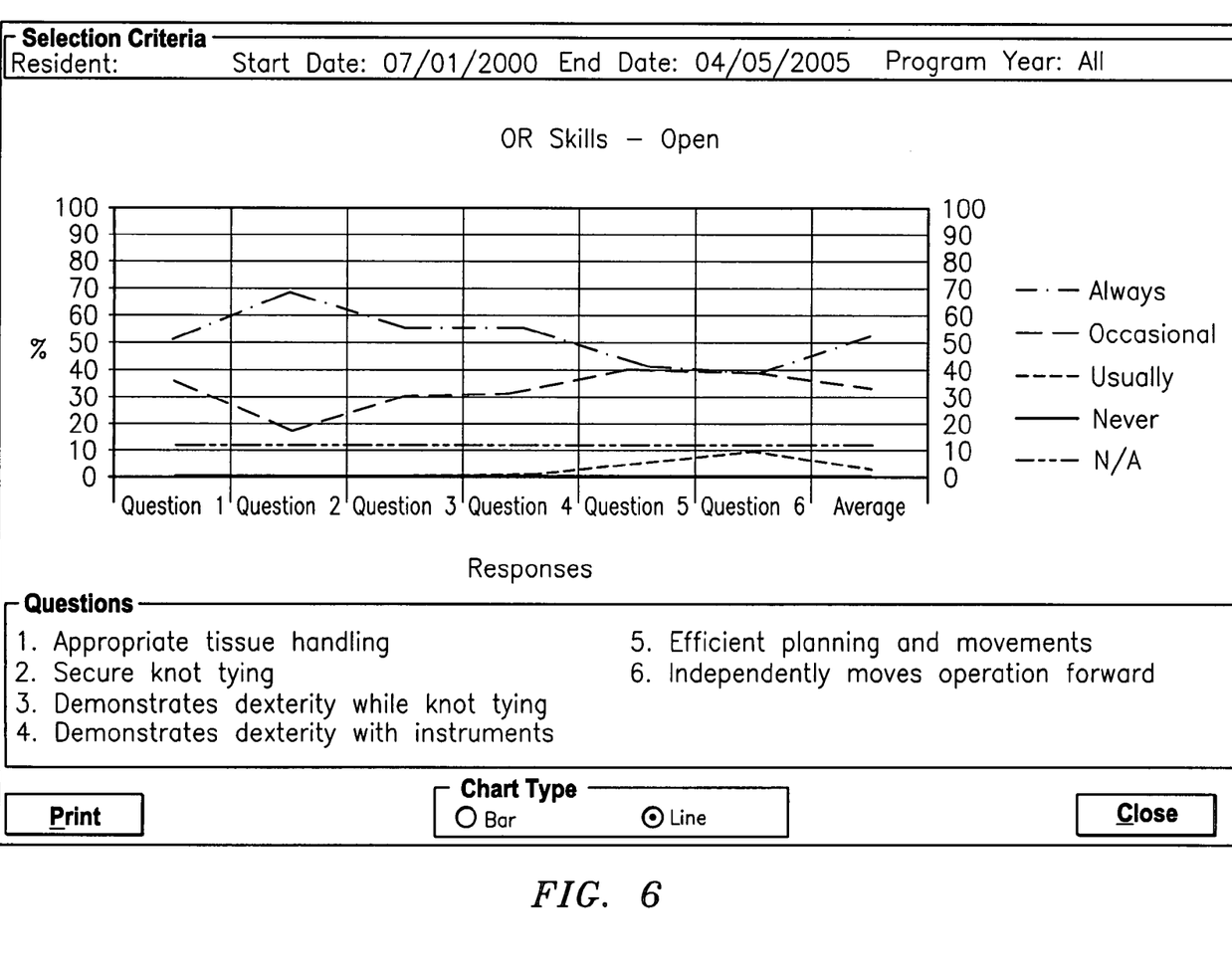
FIG. 6 illustrates a line graph generated using calculated average resident performance levels in the assessed performance categories shown in FIGS. 2, 4 and 5, which the inventive system may further generate.
Figure 7:
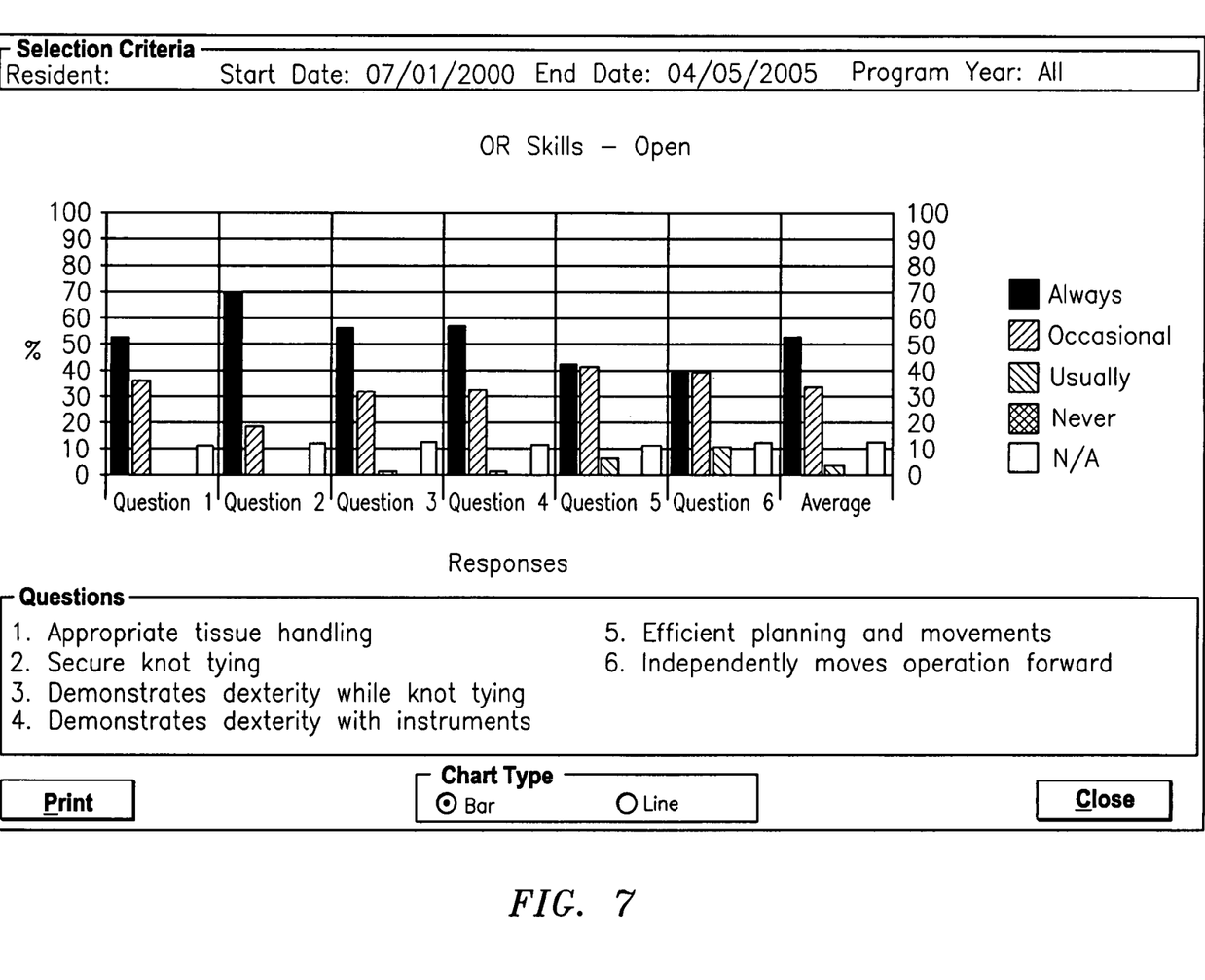
FIG. 7 illustrates a bar graph which may also be generated by the inventive system, which uses the same calculated average resident performance levels shown in FIG. 6.

By way of example, for laparoscopic procedures, assessed skills would include the level or degree of appropriate tissue handling and secure knot tying, the dexterity demonstrated by the resident while knot tying, the dexterity demonstrated with instruments, the efficiency of planning and movements, the degree to which the resident independently moved the operation forward, and the resident's equipment trouble-shooting ability. Representative forms, reports and graphs relating to laparoscopic skills assessment generated by the one or more computer programs stored in the computer(s) 14 of preferred system 10 are shown in FIGS. 2 to 7. In particular, FIG. 2 illustrates a user interface screen display in the form of a resident evaluation form or questionnaire listing the laparoscopic skills assessment areas identified above, which would be completed by a trained surgeon after overseeing a resident-assisted surgical procedure. FIG. 3 illustrates a report generated by preferred system 10, obtained by field searching a trained surgeon's last name, and showing a list of resident-assisted surgical procedures supervised by that trained surgeon. FIG. 4 illustrates a blank resident report form containing "resident name" and "date range" fields for searching. Upon executing the search, system 10 would calculate and display average performance levels in assessed performance categories. FIG. 5 illustrates an alternative presentation or display of the calculated average resident performance levels, which may also be generated by the present inventive system, while FIGS. 6 and 7 illustrate a line graph and a bar graph, respectively, both generated using calculated average resident performance levels in the assessed performance categories shown in FIGS. 2, 4 and 5. Other contemplated presentations or displays include, but are not limited to, charts, case log reports by resident name and date range, and case log report summaries categorized by the type of surgical procedure performed by the resident.

In a preferred embodiment, system 10 integrates one or more computer-based simulation tools or devices such as computer simulations (virtual reality), video simulations, or simulations using models, with the one or more computer-based tools or devices communicating results (i.e., measurement of resident skills) to the computer(s) 14 of inventive system 10.

Virtual reality is a computerized, three-dimensional form of simulation, which allows participants to become immersed in an artificial, yet realistic, environment and be able to use components of their senses in real time. As will be readily appreciated by those skilled in the art, simulation is particularly attractive in the field of surgery because it avoids the use of patients for skills practice and ensures that surgical trainees have had some practice before treating humans.

Figure 8:
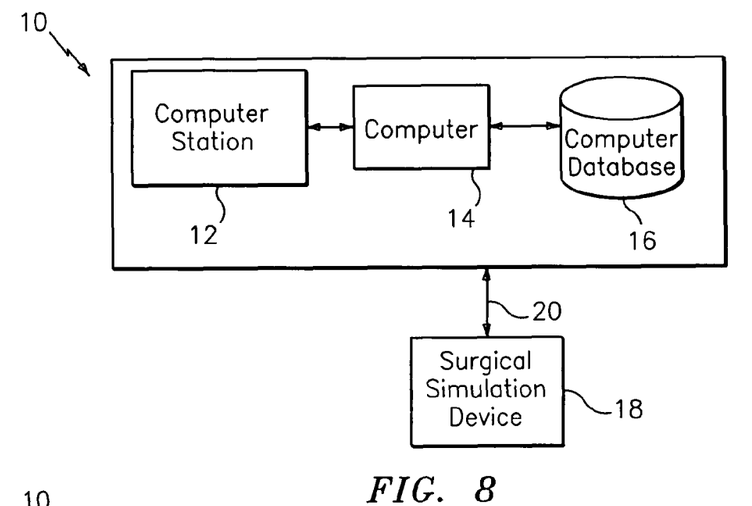
FIG. 8 is a simplified component diagram of a preferred embodiment of the system of the present invention.

In this preferred embodiment, which is best shown in FIG. 8, the inventive system 10 further comprises one or more simulation tools or devices 18 and a communications link 20 between the one or more simulation tools or devices 18 and the computer(s) 14.

In the method carried out utilizing this preferred system 10, and by way of example only, health care practitioners would undergo testing by computer simulation (e.g., MIST-VR™ virtual reality simulator, ANGIO MENTOR™, GI MENTOR™, LAP MENTOR™, PERC MENTOR™, and URO MENTOR™ computer-based simulators, PediaSIM® and BabySIM™ human patient simulators, EMERGENCY CARE SIMULATOR-ECS™ human patient simulator, and Pelvic ExamSIM™ and SurgicalSIM™ simulators) with skill strengths and weaknesses of each practitioner being assessed for each task at a defined level (e.g., easy or medium level). As simulations are performed, metrics (i.e., pieces of raw data that indicate competency levels) are collected and stored. In regard to surgical simulations, metrics may include time, efficiency of motion, errors, economy of movements, and extent of tissue damage. The metrics are used to identify skill strengths and weaknesses, which would then be communicated, via communications link 20, to the computer(s) 14 and stored in the computer database 16, allowing the health care practitioner and his/her trained educators and other educators to access the results and tailor the clinical experience to the needs of the practitioner as identified by the one or more simulation tools or devices 18.

In the embodiment described above, an information feedback loop is formed by the inventive system 10 whereby clinical and simulated clinical performance evaluations are inputted, or gathered and stored, and then made available to the health care practitioner and to his/her educator(s) throughout the health care training program thereby increasing the effectiveness of the training program by allowing the program to be continuously tailored to address the needs of the health care practitioner.

As noted above, when the inventive system 10 is used in surgical resident training programs, computer(s) 14 of system 10 may be linked via a communications link to a hospital database containing patient information for the purpose of aiding in the reduction of the risk of human error in the operating room and for monitoring, among other things, operating room efficiency and safety.

For each surgical procedure scheduled to be performed in an operating room, the method carried out utilizing the above-referenced preferred system 10 would basically comprise entering a patient identifier which identifies the patient on which the scheduled surgical procedure is to be performed into the computer station 12. If the patient identifier entered into the computer station 12 matches an identifier for that patient stored in the hospital database, the scheduled surgical procedure would be checked against the surgical procedure for that patient that is stored in the hospital database. If the scheduled surgical procedure for the patient matches the surgical procedure for that patient stored in the hospital database, then the surgical procedure on the patient would proceed. Then, for each patient on which a resident-assisted surgical procedure has been performed in the operating room, and using the patient identifier, clinical parameters such as operating room time, case cost, length of stay, complications, and the like, would be collected from the hospital database and stored in the computer database 16. Reports assessing, among other things, the operating room's efficiency and safety would then be generated and displayed and made accessible to appropriate hospital personnel.

Figure 9:
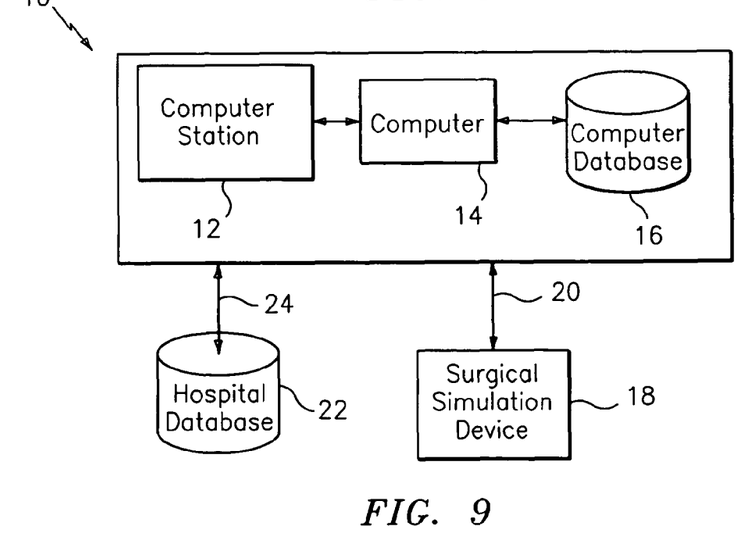
FIG. 9 is a simplified component diagram of a more preferred embodiment of the present inventive system.

In a more preferred embodiment of the present invention, which is best shown in FIG. 9, computer(s) 14 of system 10 is linked to one or more surgical simulation tools or devices 18, via communications link 20, as well as, to a hospital database 22, via a communications link 24. This more preferred system 10, and the method carried out utilizing this more preferred system 10, would allow for both the clinical operative performance evaluations and the results from the surgical simulation device(s) 18 to be used to guide resident education and training during subsequent resident-assisted surgical procedures. With the use of hospital database 22, the inventive system and method would serve to reduce the risk of human error in the operating room and to provide clinical parameters for use in assessing, among other things, the operating room's efficiency and safety, while continuing to provide timely operative performance evaluations to surgical residents and their educators.

While various embodiments of the present invention have been described above, it should be understood that they have been presented by way of example only, and not limitation. Thus, the breadth and scope of the present invention should not be limited by any of the exemplary embodiments.

Having thus described the invention, what is claimed is:

1. A computer-based method for training health care practitioners, which method comprises:
    (a) providing at least one computer station operable by trained educators for inputting their evaluations of a health care practitioner's performance of a health care or medical procedure and further operable by the health care practitioner, as well as, the trained educators and other educators, for viewing the inputted evaluations;
    (b) further providing at least one computer and at least one computer database accessible by the computer(s) for storing information including the trained educator evaluations, wherein the computer comprises memory means and one or more computer programs stored therein suitable for the management and manipulation of the information that is directed into or out of the computer database and/or stored therein;
    (c) arranging for health care practitioners to perform health care or medical procedures on patients in the physical presence of a trained educator, under the trained educator's direct supervision;
    (d) evaluating each practitioner's performance in terms of cognitive skills for treating the patient including the extent to which the practitioner was informed about the patient and technical and disease related issues pertaining to the patient and the practitioner's clinical skills and upon completion of each health care or medical procedure, entering the trained educator's evaluation of the practitioner's performance at the computer station and storing the evaluation in the computer database such that the evaluation is accessible by the practitioner;
    (e) for each such practitioner, using stored evaluations to continually customize future training for the practitioner to focus on any weaknesses or problem areas observed during each health care or medical procedure performed by the practitioner;
    (f) for each such practitioner, generating and displaying reports showing the practitioner's performance trends over time; and optionally,
    (g) for each group or team of such practitioners, generating and displaying reports showing the practitioner group or team's performance trends over time.

2. The computer-based method of claim 1, which further comprises: providing a communications link between the computer(s) and one or more simulation tools or devices used by the practitioners; arranging for practitioners to use the one or more simulation devices; importing results from the one or more simulation devices used by the practitioners into the computer(s) and storing same in the computer database(s), such that the results are accessible by the practitioners, the trained educators and other educators; and using the results from the one or more simulation devices to customize future training for the practitioner to focus on any weaknesses or problem areas identified while the practitioner was using the one or more simulation devices.

3. The computer-based method of claim 2, wherein the one or more simulation devices are selected from the group of computer simulations or virtual reality, video simulations, simulations using models, and combinations thereof.

4. The computer-based method of claim 1, wherein the method comprises providing a plurality of computer stations.

5. The computer-based method of claim 4, wherein the method is an Intranet-based method.

6. The computer-based method of claim 1, wherein the at least one computer is a server computer that acts as a gateway for Internet access.

7. The computer-based method of claim 6, wherein the server computer(s) is adapted to support a website that allows for remote access to the server computer(s) and the computer database.

8. A computer-based method for training surgical residents, which method comprises:
    (a) providing at least one computer station operable by trained surgeons for inputting their evaluations of the operative performance of surgical residents and further operable by surgical residents, as well as, the trained surgeons and other educators, for viewing the inputted evaluations;

(b) further providing at least one computer and at least one computer database accessible by the computer(s) for storing information including the trained surgeon evaluations, wherein the computer comprises memory means and one or more computer programs stored therein suitable for the management and manipulation of the information that is directed into or out of the computer database and/or stored therein;

(c) arranging for surgical residents to perform surgical procedures on patients in the physical presence of a trained surgeon, under the trained surgeon's direct supervision;

(d) evaluating each surgical resident's operative performance in terms of cognitive skills for treating the patient including the extent to which the resident was informed about the patient and technical and disease related issues pertaining to the patient and the resident's operative skills during each such surgical procedure and upon completion of each procedure, entering the trained surgeon's evaluation of the resident's operative performance at the computer station and storing the evaluation in the computer database such that the evaluation is accessible by the surgical resident;

(e) for each such surgical resident, using stored evaluations to continually customize future training for the resident to focus on any weaknesses or problem areas identified during each surgical procedure performed by the resident;

(f) for each such surgical resident, generating and displaying reports showing the resident's performance trends over time; and optionally, (g) for each group or team of such surgical residents, generating and displaying reports showing the resident group or team's performance trends over time.

9. The computer-based method of claim 8, which further comprises: providing a communications link between the computer(s) and one or more surgical simulation tools or devices used by the surgical residents; arranging for surgical residents to use the one or more surgical simulation devices; importing results from the one or more surgical simulation devices used by the surgical residents into the computer(s) and storing same in the computer database(s), such that the results are accessible by the residents, the trained surgeons and other educators; and using the results from the one or more surgical simulation devices to customize future training for the resident to focus on any weaknesses or problem areas identified while the resident was using the one or more surgical simulation devices.

10. The computer-based method of claim 9, wherein the one or more surgical simulation devices are selected from the group of computer simulations or virtual reality, video simulations, simulations using models, and combinations thereof.

11. The computer-based method of claim 8, which further comprises:

(a) providing a communications link between the computer(s) and a hospital database containing patient information; and for each surgical procedure scheduled to be performed in an operating room, (b) entering into the computer station a patient identifier which identifies the patient on which the scheduled surgical procedure is to be performed; and if the patient identifier entered into the computer station matches an identifier for that patient stored in the hospital database, (c) checking the scheduled surgical procedure against the surgical procedure for that patient that is stored in the hospital database; and if the scheduled surgical procedure for the patient matches the surgical procedure for that patient stored in the hospital database, (d) performing the surgical procedure on the patient.

12. The computer-based method of claim 11, wherein for each patient on which a resident-assisted surgical procedure has been performed in the operating room, and using the patient identifier, said method further comprising: collecting from the hospital database clinical parameters such as operating room time, case cost, length of stay, and complications; storing this information in the computer database; and generating and displaying reports assessing the operating room's efficiency and safety.

13. The computer-based method of claim 8, which further comprises providing a communications link between the computer(s) and a hospital database containing patient information.

14. The computer-based method of claim 8, wherein the method comprises providing a plurality of computer stations.

15. The computer-based method of claim 14, wherein the method is an Intranet-based method.

16. The computer-based method of claim 8, wherein the at least one computer is a server computer that acts as a gateway for Internet access.

17. The computer-based method of claim 16, wherein the server computer(s) is adapted to support a website that allows for remote access to the server computer(s) and the computer database.

18. The computer-based method for training surgical residents of claim 8, wherein the evaluated operative skills are selected from the group of tissue handling skills, knot tying skills, instrument handling skills, planning and implementation skills, leadership skills, and equipment troubleshooting skills.

19. The computer-based method for training surgical residents of claim 8, wherein the surgical procedures performed by the surgical residents are laparoscopic procedures, and wherein the evaluated operative skills include the resident's level or degree of (a) appropriate tissue handling and secure knot tying, (b) dexterity while knot tying, (c) dexterity with instruments, (d) efficiency of planning and movements, (e) independently moving the surgical procedure forward, and (f) equipment trouble-shooting ability.

* * * * *